United States Patent [19]

Yen et al.

[11] Patent Number: 5,242,672
[45] Date of Patent: Sep. 7, 1993

[54] PROCESS FOR REMOVING SULFUR FROM ORGANIC POLYSULFIDES

[75] Inventors: Jeffrey H. Yen, Woolwich, N.J.; Glenn T. Carroll, Jeffersonville, Pa.; Vijay R. Srinivas, Uwchlan, Pa.; William J. Tuszynski, Milford Township, Bucks County, Pa.; John A. Wismer, Devon, Pa.

[73] Assignee: Elf Atochem North America, Inc., Philadelphia, Pa.

[21] Appl. No.: 188,863

[22] Filed: May 2, 1988

Related U.S. Application Data

[63] Continuation-in-part of Ser. No. 878,163, Jun. 25, 1986, abandoned.

[51] Int. Cl.$^5$ .................. C01B 17/20; E21B 37/06
[52] U.S. Cl. ............................ 423/562; 166/312; 208/237; 208/238; 252/8.552
[58] Field of Search ............. 423/562; 208/237, 238; 166/312; 299/5; 252/8.552

[56] References Cited

U.S. PATENT DOCUMENTS

| | | | |
|---|---|---|---|
| 3,474,028 | 10/1969 | Bulian et al. | 208/230 |
| 3,489,677 | 1/1970 | Thompson et al. | 208/236 |
| 3,617,529 | 11/1971 | Thompson et al. | 208/230 |
| 3,748,827 | 7/1973 | Bulian et al. | 55/73 |
| 3,909,422 | 9/1975 | Sample, Jr. | 252/8.552 |
| 4,018,572 | 4/1977 | Swanson | 208/230 |
| 4,033,410 | 7/1977 | Kauffman | 166/312 |
| 4,230,184 | 10/1980 | Blytas | 166/312 |
| 4,322,307 | 3/1982 | Kettner | 252/8.552 |
| 4,454,017 | 6/1984 | Swanson | 208/230 |
| 4,543,193 | 9/1985 | Peter et al. | 252/8.552 |

FOREIGN PATENT DOCUMENTS 2579203 9/1986 France.

OTHER PUBLICATIONS

*Chemical Engineers' Handbook*, 5th ed. Perry et al., eds. McGraw-Hill Book Co. 1973. pp. 21-24, 14, 26.
Muller, *Methoden Der Organischen Chemie*, 4th ed. George Thieme Varlag, 1955, vol. IX, pp. 87-92.
Dowling et al., "Regeneration of Loaded Dimethyldisulfide Based Sulfur Solvents," Alberta Sulfur Research Ltd., Quart. Bull., vol. XXI, Nos. 344, pp. 30-52 (Oct. '84-Mar. '85).

*Primary Examiner*—Jeffrey E. Russel

[57] ABSTRACT

A process for removing sulfur from an organic polysulfide by reaction with an aqueous stripping solution of at least one sulfide salt and/or hydrosulfide salt in a multistage, continuous, countercurrent flow, reaction system wherein the sulfur is stripped from the polysulfide into the aqueous stripping solution phase which is separated from the polysulfide organic phase.

5 Claims, 5 Drawing Sheets

PROCESS FOR REMOVING SULFUR FROM ORGANIC POLYSULFIDES

BACKGROUND OF THE INVENTION

This is a continuation-in-part of copending application Ser. No. 878,163 filed Jun. 25, 1986, now abandoned.

In deep sour gas wells, a solvent may be pumped down the annulus between the well casing and the production tubing in order to prevent blockage by sulfur deposition in the production string. The solvent flows back up through the production tubing along with the produced gases, is separated from the gas, and is recycled back to the well. As the solvent circulates, it absorbs a small amount of elemental sulfur which is produced by the wells. Since the solvent is recirculated, there is a continuous increase in its sulfur concentration. Dialkyl disulfides, alkyl sulfides, polysulfides, benzene, toluene, spindle oil, and the like have been used as solvents for controlling sulfur deposition. In order for this process to be economical, it is desirable to remove the sulfur from the solvent so that the solvent can be recycled downhole.

Many processes in the prior art are known for the extraction of dissolved sulfur from solvents. U.S. Pat. Nos. 3,474,028, 3,489,677, 3,617,529, 3,748,827, 4,018,572, and 4,230,184 disclose the use of alkali metal and ammonium hydrosulfides and sulfides to remove dissolved sulfur from mineral oils. The publication of Dowling, Lesage, and Hyne ("Regeneration of Loaded Dimethyl Disulfide Based Sulfur Solvents", Alberta Sulfur Research Limited Quarterly Bulletin, Vol. XXI, No. 3 and 4, pp. 30-52, October 1984-March 1985) discloses the regeneration of dimethyl disulfide by stripping sulfur from dimethyl polysulfide in a batch operation with alkali metal ammonium hydrosulfides and sulfides, preferably sodium sulfide. None of the above prior art references discloses the instant invention of a continuous multistage countercurrent flow reaction system.

SUMMARY OF THE INVENTION

The present invention is directed to a process of removing, in a multi-stage system, sulfur from a stream of an organic polysulfide of high sulfur rank comprising, (a) continuously contacting said stream of organic polysulfide with a stream of an immiscible metallic sulfide or hydrosulfide salt containing aqueous stripping solution which passes through said system counter-currently to said stream of organic polysulfide, said contacting occurring by intimately mixing said streams in at least two successive, direct-contact stages to form at each such stage an aqueous phase of increased sulfur content and an organic phase containing a polysulfide of lower sulfur rank, (b) separating the aqueous phase of increased sulfur content and the organic phase of lower rank polysulfide between each direct contact stage and thereafter directing each phase to a different stage until all stages of the system are traversed, said aqueous phase always directed to a stage containing an organic phase of a polysulfide of sulfur rank higher than that in the stage already traversed, and (c) recovering the polysulfide of low sulfur rank after traversal of the last stage by the organic phase.

Sulfur may be recovered from the aqueous stripping solution after traversal of the last stage by the aqueous phase or the aqueous phase may be discarded.

DETAILED DESCRIPTION OF THE INVENTION

Although the process is illustrated herein by dimethyl polysulfide as the sulfur bearing organic component requiring desulfurization and aqueous sodium sulfide as the stripping solution, the invention broadly is a process for the removal of sulfur from an organic polysulfide, and/or its mixtures, by contacting it with an aqueous solution of one or more sulfide salts and/or hydrosulfide salts of the formula $Y_2S$ or $ZSH$ wherein Y is selected from Group IA of the Periodic Table and a member of the group $NR_1R_2R_3R_4$ where $R_1$, $R_2$, $R_3$ and $R_4$ are independently selected from H, and alkyl of 1-20 carbons (such as methyl, butyl, cyclohexyl, and cetyl), aryl of 6-14 carbons (such as phenyl, naphthyl, and anthracenyl), and alkylaryl of 7-34 carbons (such as tolyl, dodecylphenyl, cetylphenyl, butylnaphthyl, and butylanthracenyl). Z is selected from Y and Group IIA of the Periodic Table.

The reaction is carried out in a multi-stage, direct-contact, countercurrent, continuous flow reactor system such that said aqueous sulfide salt and/or hydrosulfide salt chemically reacts with said organic polysulfide to give an aqueous polysulfide solution and an organic polysulfide of lower sulfur rank, i.e., a polysulfide wherein fewer sulfur atoms are present in each polysulfide molecule. The polysulfide, in this case, will include the disulfide. The chemical reaction is depicted by the following equation (1):

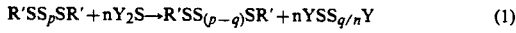

$$R'SS_pSR' + nY_2S \rightarrow R'SS_{(p-q)}SR' + nYSS_{q/n}Y \qquad (1)$$

where $p > 0$ and $q \leq p$.

Temperature and pressure do not materially affect the performance of the process while operation at ambient conditions is preferred. Key parameters which must be considered are the selection and concentration of the aqueous stripping solution, period of contact, and the molar ratio of the sulfide salt and/or hydrosulfide salt to recoverable sulfur in the organic polysulfide. The recoverable sulfur is the sulfur above rank two that is chemically incorporated into the organic polysulfide. The rank is defined as the average number of sulfur atoms in the organic polysulfide molecule. These parameters are constrained by the requirement that the difference in the densities of the organic and aqueous phases in each separation zone be sufficient to allow efficient phase separation. The density difference can be enhanced by adding into the organic polysulfide a miscible liquid solvent with a density lower than that of the organic polysulfide.

Figure 1:
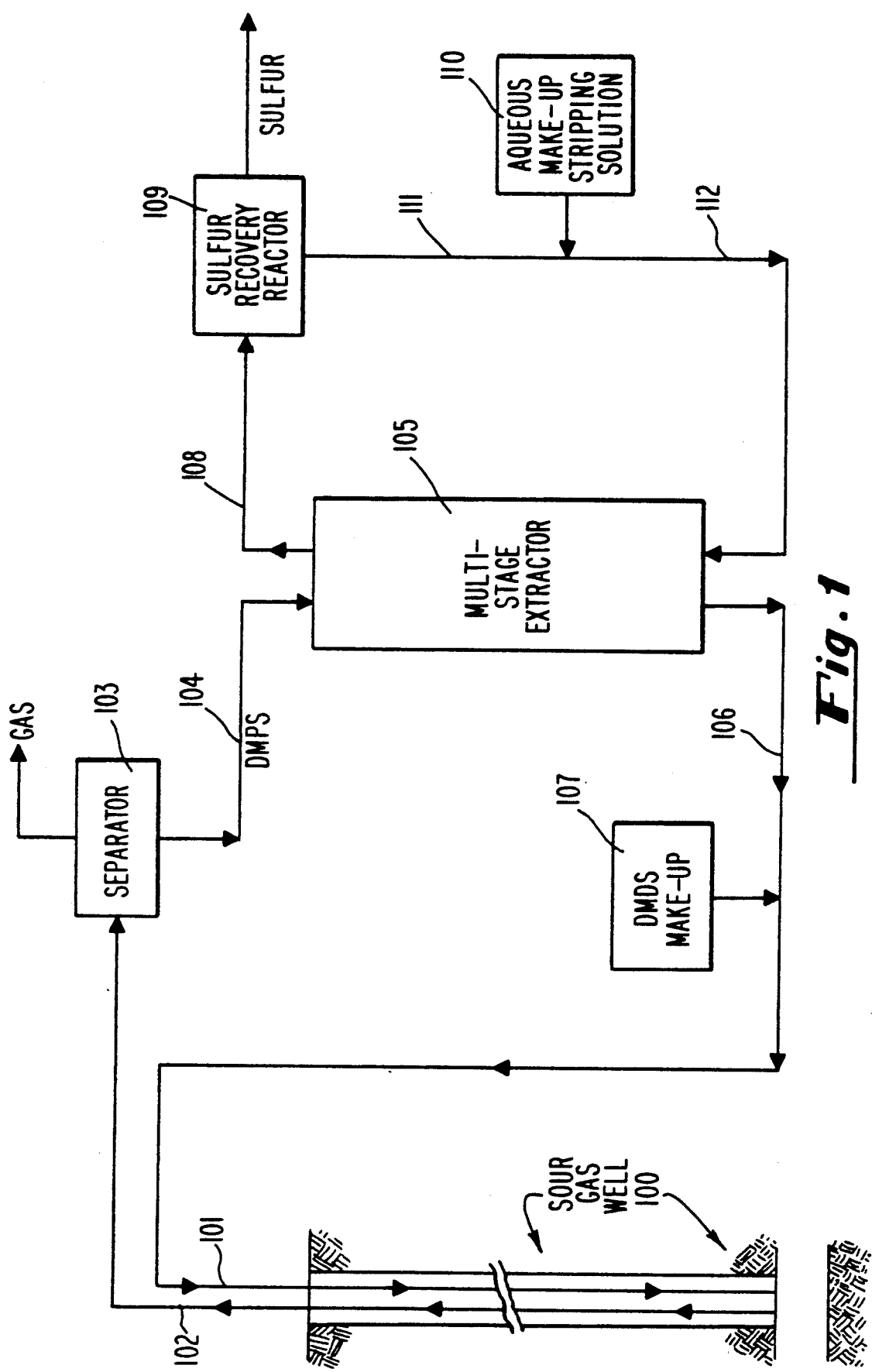
FIG. 1 is a flow sheet of a process for removing sulfur from a sour gas well.
Figure 2:
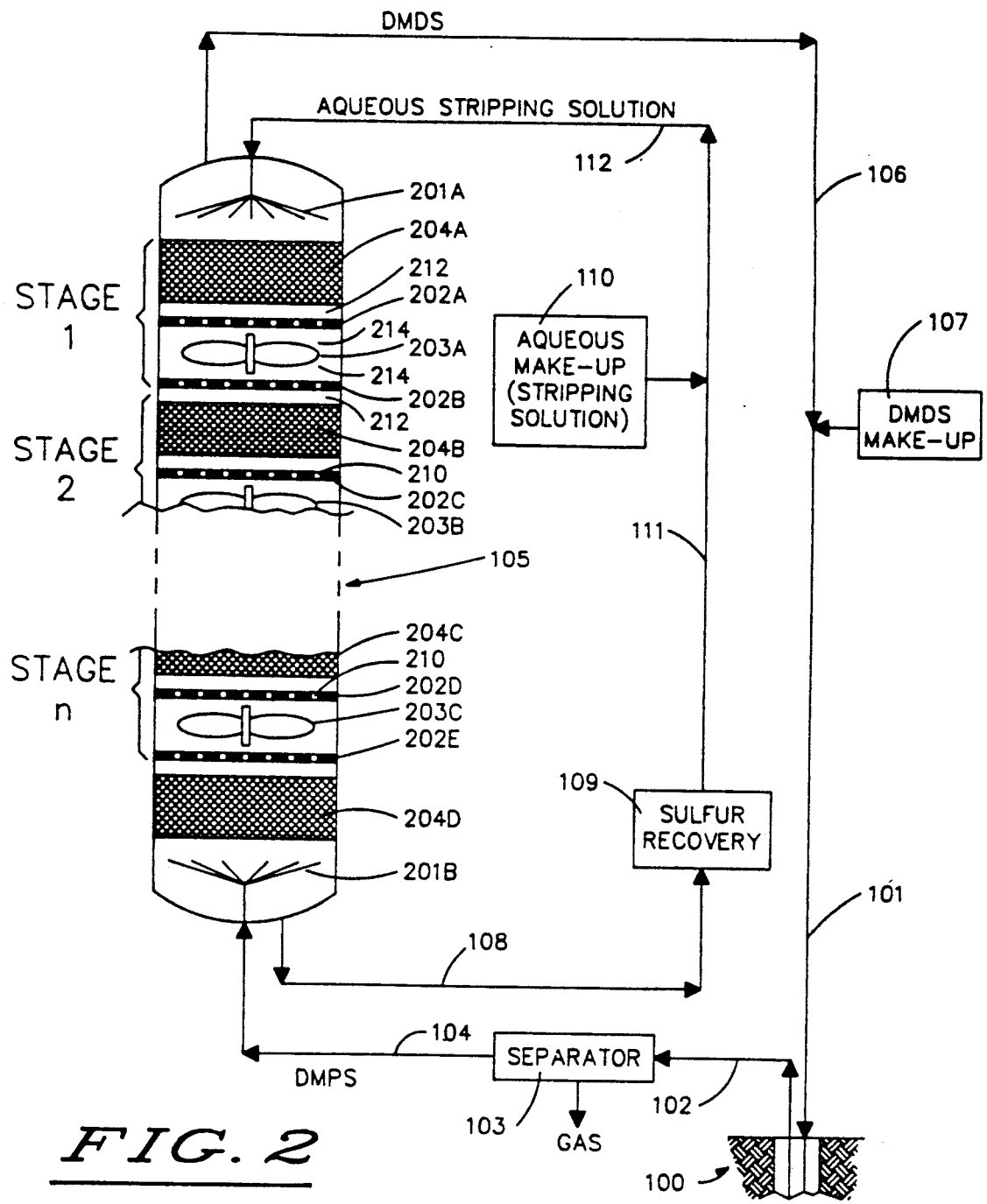
FIG. 2 illustrates a multi-stage countercurrent flow vertical column useful in the process of the present invention.
Figure 3:
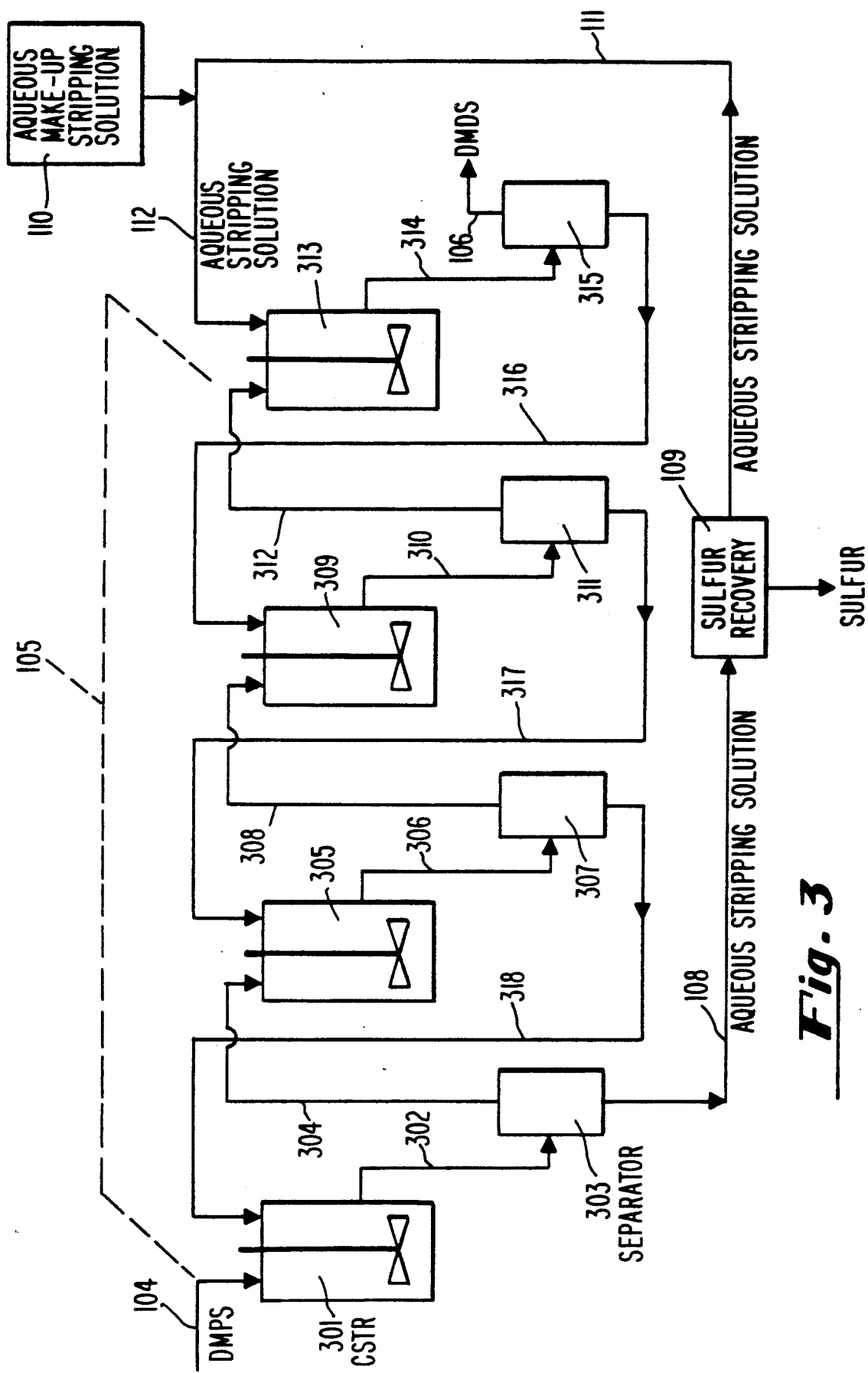
FIG. 3 is a flow sheet of a process for removing sulfur from an organic polysulfide using a series of reactor tanks and separators in the sulfur removal process.

In FIGS. 1, 2 and 3, like-numbered elements of the figures are the same. FIG. 1 is a schematic flowsheet illustrating a system for sulfur removal from a sour gas well. In the processing of a sour gas well 100, sulfur often forms deposits that may plug the well and interrupt production. Such deposits may be removed by introducing a solvent for sulfur [such as dimethyl disulfide (DMDS)] downhole via line 101, optionally in the presence of a catalyst such as dimethyl formamide and sodium hydrosulfide, as is well known in the art. Riser pipe 102 delivers the gas and organic polysulfide (formed by reaction of the sulfur with the DMDS) from the well bottom to separator 103 where the gas is removed from the organic polysulfide (DMPS). The gas (which is usually a mixture largely of methane, hydrogen sulfide, and carbon dioxide) is treated to separate the components and to convert the hydrogen sulfide to elemental sulfur via the well known Claus technology. The DMPS is passed via line 104 to multi-stage stripping reactor represented schematically at 105 to separate elemental sulfur from the DMDS which is returned to the well via lines 106 and 101 for reuse in well 100. Optionally, prior to entering reactor 105, the DMPS is mixed with a miscible, liquid solvent having a density lower than that of the DMPS. Make-up DMDS (and optionally catalyst) may be added at 107 to the regenerated DMDS from reactor (or extractor) 105 to replace materials lost in processing. An aqueous stripping solution (such as sodium sulfide) is added to reactor 105 in a countercurrent flow via line 112 and, as it passes countercurrently through and reacts with the polysulfide in reactor 105, its sulfur content increases. The sulfur-laden aqueous stripping solution is discharged via line 108 to sulfur recovery system 109. Optionally, the sulfur is removed in sulfur recovery system 109 and the aqueous stripping solution may be returned via lines 111 and 112 to reactor 105. Make-up stripping solution at 110 may be added to the recycled stripping solution in lines 111 and 112 to replace material lost in processing.

The multi-stage countercurrent flow reactor 105 may be in the form of a vertical multistage column as shown in FIG. 2 which has separate stages therein with top and bottom distributors 201A and 201B, redistributor plates 202A, 202B, 202C, 202D and 202E, agitators 203A, 203B and 203C and packing sections 204A, 204B, 204C and 204D for ultimate countercurrent flow direct contact and separation. Packing section 204A, redistributor plate 202A, agitator 203A, and redistributor plate 202B comprise stage 1 of the reactor column 105. Similar components will form the nth stage in the column as shown in FIG. 2. The circular redistribution plates 202 are provided with spaced orifices (or holes) 210 therethrough. The DMPS (organic) phase is pumped into the bottom of the multistage column via line 104 while the fresh aqueous stripping solution, via lines 111 and 112, flows into the top of column 105. The aqueous stripping solution is evenly distributed cross-sectionally with the aid of a distributor 201A and similarly with the DMPS at the bottom end of the reactor column 105 by distributor 201B; the aqueous stripping solution starts to contact the sulfur-laden organic phase at the top of column. The organic phase has a relatively lower sulfur content at the top as compared to the bottom of the column. Since the foreign sulfur content in the aqueous stripping solution is almost zero at the top of the column, the driving potential (i.e., the tendency of the chemical reaction of equation (1) to proceed from left to right) for transferring the residual recoverable sulfur from the organic phase to the aqueous phase is expected to be reasonably high. The "foreign sulfur" is the recoverable sulfur which has been transferred from the organic phase to the aqueous stripping phase.

After initial contact, the aqueous stripping solution and the organic phase continue to pass and contact each other countercurrently in the packing section 204A, 204B, 204C and 204D. The packing sections are essential to phase separation. After the packing section 204B, the aqueous stripping solution flows through redistributor 202C into an agitation section where both phases are stirred and mixed by agitator 203B. The agitation speed is controlled and space 214 is reserved between the redistributors 202 and the agitators 203 and space 212 optionally positioned between redistributor plates 202 and packing sections 204 such that the continuous upward and downward flows are maintained. Spaces 212 and 214 render the entire extraction process more efficient. The aqueous stripping solution continues to flow through the next stage including a redistributor, an agitation zone, a packing section, and a redistributor. A number of stages can be added thereafter depending on the process needs.

Finally, the aqueous stripping solution with a high foreign sulfur loading reaches the bottom of the column 105 where the recoverable sulfur content in the organic phase is the highest throughout the column. At this point, a driving potential still exists between the aqueous stripping solution and the organic phase because of the relative concentration of sulfur in the two liquids. The sulfur-laden aqueous stripping solution is discharged from the bottom of the column via line 108 for disposal or, optionally, for further treatment. The sulfur can be recovered from the sulfur-laden aqueous stripping solution by conventional means such as neutralization with acids and cryogenic procedures to precipitate the sulfur from the solution.

The organic phase has a flow pattern similar to the aqueous stripping solution except the organic phase flows upward. If the density of the organic phase is heavier than that of the aqueous stripping solution, the above-mentioned flow pattern will be reversed.

As shown in the embodiment of FIG. 3, each stage of the reactor system also can be in the form of a separate reactor tank 301, 305, 309, 313 with a stirrer therein and a conduit 302, 306, 310, 314 connecting each reactor tank to a separate phase separator tank 303, 307, 311, 315 where each stage is connected in series such that the organic phase from the first separator 303 will go directly into the second stage reactor tank 305 via line 304 and the organic phase from the second separator 307 should go into reactor tank 309 of the third stage via line 308 and the organic phase from the third separator 311 will go into tank 313 via line 312 and so on and so forth until the organic phase from final separator 315 is the regenerated (i.e., lower rank sulfur content polysulfide) product via line 106; and the stripping solution from each separator 307, 311, 315 is returned via lines 318, 317, 316 to the previous reactor stage 301, 305, 309 to be the stripping solution therein. In stage 313 fresh stripping solution is added thereto via lines 111 and 112 from aqueous make-up stripping solution 110 to flow countercurrently to and react with the DMPS and thereafter to follow the flow pattern described above. Aqueous stripping solution containing foreign sulfur is removed from separator 303 via line 108 to be disposed of or to optionally be sent to a sulfur recovery system 109 where sulfur is removed from the aqueous stripping solution; the aqueous stripping solution may then be returned to reactor 313 via lines 111 and 112. Obviously, if the density of the organic phase is heavier than that of the aqueous stripping solution, the above-mentioned flow pattern will be reversed.

The preferred number of stages in either system is a function of the degree of regeneration and recovery required; in most cases, two stages are sufficient.

Among the sulfide salts and/or hydrosulfide salts suitable for use in the present invention, sodium sulfide in water is preferred, preferably at a concentration of between 10 weight percent and the saturation concentration of sodium sulfide at the operating temperature of the system.

The preferred reaction times (defined as the total liquid volume flow rate of the organic and aqueous phases divided into the sum of the available reaction volumes in the reactors) range from 5 to 120 minutes; generally the operation is complete in 30 minutes. At contact times shorter than 5 minutes regeneration is insufficient while contact times longer than 120 minutes do not result in significantly improved regeneration.

The molar ratio of the sulfide salt and/or hydrosulfide salt in the aqueous solution to the recoverable sulfur in the DMPS (R value) may range from 0.10 to 0.70; the preferred range is 0.20 to 0.40. Using R values below 0.10 result in incomplete regeneration while using R values above 0.70 result in decreased recovery of the DMPS.

The DMPS does not have to originate from the downhole cleaning of a sour gas well. In the preparation of lower organic disulfides, the disulfides are frequently separated from their co-produced polysulfides by distillation. However, it is often not feasible to purify higher organic disulfides (e.g., butyl, hexyl, nonyl, aryl, etc.) by distillation because of decomposition and the process of this invention can be employed to produce higher organic disulfides from their respective polysulfides.

EXAMPLE 1

Employing the system of FIG. 3, DMPS containing 46.8 weight % recoverable sulfur was reacted with a 15% aqueous solution of sodium sulfide in a continuous, countercurrent flow, direct contact two-stage system for a total of 20 minutes in the system. The molar ratio of the sodium sulfide to recoverable sulfur was 0.24. Values of 79% regeneration and 94% recovery were obtained.

For the sake of comparison, the same experiment was repeated except that a continuous single stage system was used in place of the multi-stage, countercurrent flow, direct contact system. The molar ratio of sodium sulfide to recoverable sulfur and the contact time for this experiment were 0.24 and 15 minutes, respectfully. Values of 58% regeneration and 88% recovery were obtained. Thus, the countercurrent, multi-stage technique of the present invention not only increased the percent regeneration but also increased the percent recovery resulting in substantial savings.

Percent regeneration and percent recovery are defined as follows:

$$\% \text{ Regeneration} = \frac{(\text{wt. \% } S_R \text{ in Feed}) \times F - (\text{wt. \% } S_R \text{ in Effluent}) \times E}{(\text{wt. \% } S_R \text{ in Feed}) \times F} \times 100\%$$

$$\% \text{ Recovery} = \frac{\text{wt. } DMDS \text{ (out)}}{\text{wt. } DMDS \text{ (in)}} \times 100\%$$

where $S_R$ is the sulfur that has been chemically and/or physically incorporated into the DMPS, F is the flow rate of the organic feed, and E the flow rate of the organic effluent.

In order to show that the slightly lower contact time used above in the single stage system had little or no effect, the result of an additional experiment is presented where the contact time was 29 minutes and the molar ratio of sodium sulfide to recoverable sulfur was 0.24. Values of 57% regeneration and 89% recovery were obtained. The results and process conditions of Example 1 are given in Table 1.

TABLE 1

|  | Single Stage Process | | Two-Stage Countercurrent Process |
|---|---|---|---|
| R | 0.24 | 0.24 | 0.24 |
| Contact Time | 15 Min. | 29 Min. | 20 Min. |
| % Regeneration | 58% | 57% | 79% |
| % Recovery | 88% | 89% | 94% |

EXAMPLE 2

Figure 4:
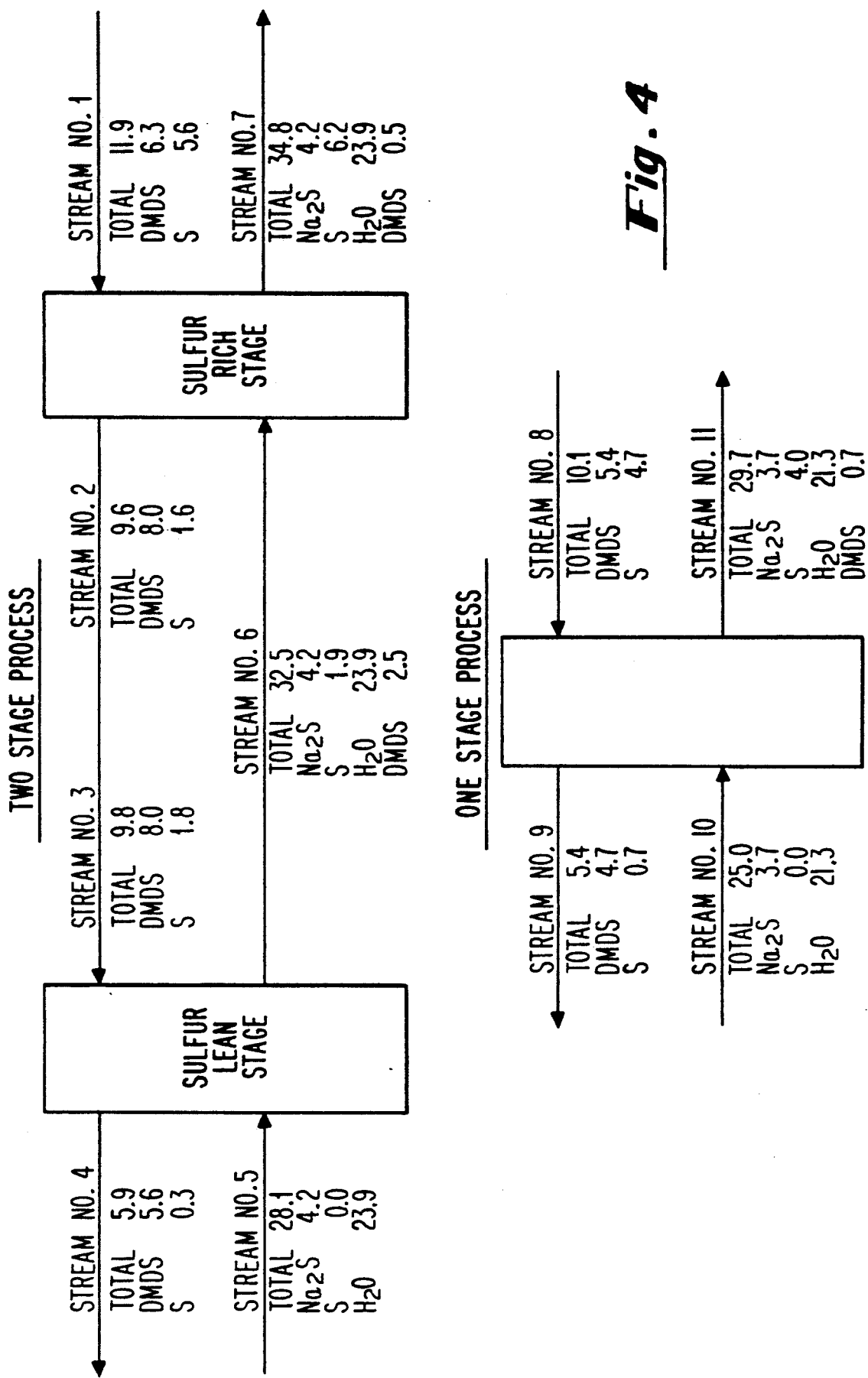
FIG. 4 is a diagram of a one stage process vs. a two stage countercurrent process wherein $R = 0.32 \pm 0.01$.

The two stage countercurrent system was evaluated, as shown in FIG. 4, using equipment geometry consistent with the intended commercial practice. Specifically, a 1 gallon (3675 ml liquid hold-up) autoclave was coupled with a horizontally configured settler (6 in. diameter by 18 in. length). As depicted in the upper diagram of FIG. 4, the two stage system was simulated by doing two separate one stage experiments. In FIG. 4, the nominal R value is 0.32±0.01 and all flow rates are in pounds per hour. First, a DMPS feed using a sulfur loading consistent with the effluent from the sulfur rich stage (Stream 2) was fed to the reactor with a 15% Na$_2$S solution. The effluent streams from the decanter were sampled and analyzed. The aqueous effluent (Stream 6) was then fed to the sulfur rich stage with 88% sulfur loaded DMPS feed. The experiment was designed to yield an organic effluent (Stream 2) which was close in composition and flow rate to the sulfur lean stage feed (Stream 3). The mass balances were converged by trial and error experimentation. For an R value of 0.31 the analyzed compositions and measured flow rates for all of these streams are shown in FIG. 4. For an R value of 0.31, the % Recovery (as measured by the DMDS lost in Stream 7) was 92.0, and the % Regeneration was 94.6. For comparison, a one stage experiment was run using an R value of 0.327. The % Recovery using the same DMDS loss criteria was 84.0 with a % Regeneration of 85.1.

EXAMPLE 3

Figure 5:
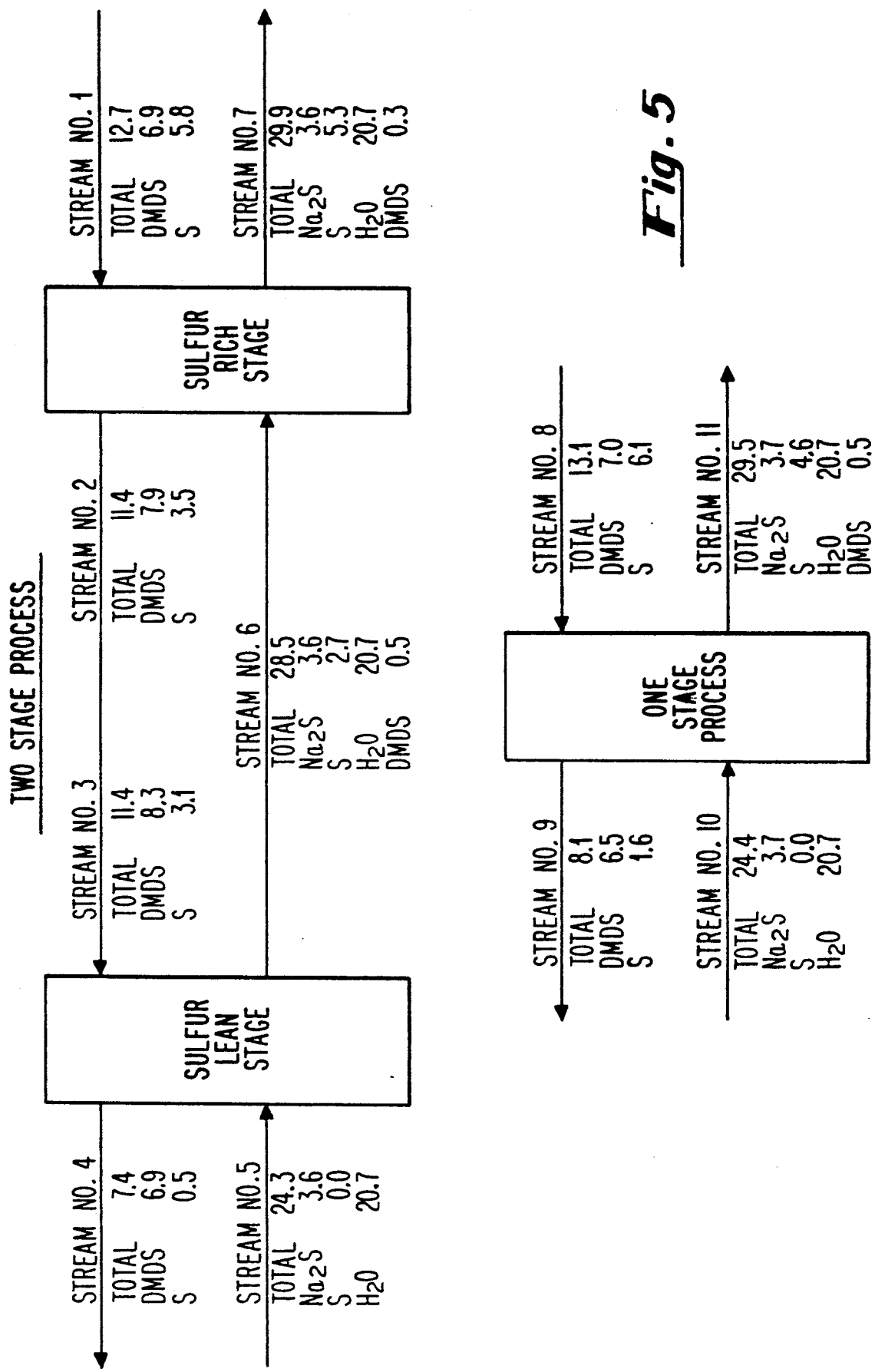
FIG. 5 is a diagram of a one stage process vs. a two stage countercurrent process wherein $R = 0.25$.

Example 2 was repeated using a nominal R value of 0.25 (FIG. 5). At this R value, the separation was very poor since the effective densities of the aqueous and organic effluents from the sulfur rich stage were almost equal (1.22 g/ml). In a commercial sized settler, a density difference of less than 0.01 g/ml can be considered inoperable. As a result, kerosene solvent was added with the DMPS feed (Stream 3) in the sulfur rich stage in the ratio of 1 part kerosene (0.82 g/ml) per 9 parts DMPS. The result was an aqueous layer density of 1.23 g/ml and an organic layer density of 1.16 g/ml. When the kerosene ratio was lowered to 1 part per 19 parts of DMPS, the organic phase density increased to 1.19 g/ml but the system remained operable. FIG. 5 shows a material balance (as analyzed) and flow rates (as measured in pounds per hour) for the two stage simulation exclusive of kerosene which can be considered an inert. The % Recovery as measured by loss in the aqueous phase was 96.0 and the % Regeneration was 81.4. By comparison, a one stage run evaluated by the same criteria shows a % Recovery of 92.3 and a % Regeneration of 73.7.

What is claimed:

1. A process of removing, in a multi-stage system, sulfur from a stream of a dialkyl polysulfide of high sulfur rank comprising,
   a) continuously contacting a stream of a mixture of dialkyl polysulfide and a liquid solvent, said liquid solvent chosen and used in amounts such that the density of said mixture is at least 0.01 g/ml less than the density of the aqueous stripping solution, with a stream of an immiscible metallic sulfide or hydrosulfide salt containing aqueous stripping solution which passes through said system countercurrently to said stream of said mixture, said contacting occurring by intimately mixing said streams in at least two successive, direct-contact stages to form at each such stage an aqueous phase of increased sulfur content and an organic phase containing a dialkyl polysulfide of lower sulfur rank,
   b) separating the aqueous phase of increased sulfur content and the organic phase of lower sulfur rank polysulfide between each direct contact stage and thereafter directing each phase to a different stage until all stages of the system are traversed, said aqueous phase always directed to a stage containing a dialkyl polysulfide of sulfur rank higher than that in the stage already traversed, and
   c) recovering the dialkyl polysulfide of low sulfur rank after traversal of the last stage by the organic phase.

2. The process of claim 1 wherein said dialkyl polysulfide is dimethyl polysulfide.

3. The process of claim 1 wherein said liquid solvent is selected from the group consisting of paraffins, olefins, aromatics, ethers, ketones, aldehydes, alcohols, and their mixtures.

4. The process of claim 1 wherein said liquid solvent is kerosene.

5. The process of claim 1 wherein the weight percentage of said liquid solvent in the mixture is from 2% to 90%.

* * * * *